(12) United States Patent
Kochat et al.

(10) Patent No.: US 6,977,311 B2
(45) Date of Patent: Dec. 20, 2005

(54) PROCESS FOR SYNTHESIZING L-γ-METHYLENE GLUTAMIC ACID AND ANALOGS

(75) Inventors: Harry Kochat, San Antonio, TX (US); Xinghai Chen, San Antonio, TX (US); Ye Wu, Helotes, TX (US); Qiuli Huang, San Antonio, TX (US); Jianyan Wang, Helotes, TX (US); Vincent Gerusz, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 8 days.

(21) Appl. No.: 10/627,484

(22) Filed: Jul. 25, 2003

(65) Prior Publication Data

US 2004/0106826 A1 Jun. 3, 2004

Related U.S. Application Data

(60) Provisional application No. 60/421,489, filed on Oct. 25, 2002.

(51) Int. Cl.[7] .................. C07C 229/00; C07D 209/46
(52) U.S. Cl. ................... 562/571; 562/573; 548/472
(58) Field of Search .................... 548/472; 562/571, 562/573

(56) References Cited

U.S. PATENT DOCUMENTS 4,996,207 A    2/1991  Nair et al.
5,550,128 A    8/1996  Nair et al.

OTHER PUBLICATIONS

Ezquerra et al, Efficient synthesis of 4–methylene–L–glutamic acid and its cyclopropyl analog, 1994, 5(5), p. 921–6.*

Kristensen et al., "Synthesis and Properties of Hydroxylated and Alkylated Acidic Amino Acids, Especially Glutamic Acid" *ACTA Chemica Scandinavica, Series B: Organic Chemistry and Biochemistry,* B34(7):497–504 (1980).

Powell et al., "A Modified High Yield Procedure for the Synthesis of Unlabeled and Carbon 14–Labeled 4–Methylene–DL–Glutamic Acid," *Preparative Biochemistry,* 11(3):339–350 (1981); and.

Boggs et al., "Chemical Modification of Peptides Containing alpha–Carboxyglutamic Acid," *J. Org. Chem.,* 47(10):1812–1816 (1982).

* cited by examiner

*Primary Examiner*—Cecilia J. Tsang
*Assistant Examiner*—Taylor V. Oh
(74) *Attorney, Agent, or Firm*—Akin Gump Strauss Hauer & Feld, LLP

(57) ABSTRACT

A process for synthesizing substantially enantiomerically pure L-amino acids, particularly L-γ-methylene glutamic acid, and esters and salts thereof. The process includes the derivatization of (2S)-pyroglutamic acid, and the decyclization of the resulting derivative to form the desired end product.

5 Claims, No Drawings

PROCESS FOR SYNTHESIZING L-γ-METHYLENE GLUTAMIC ACID AND ANALOGS

CROSS REFERENCE TO RELATED APPLICATIONS

This application claims the benefit of U.S. Provisional application, Ser. No. 60/421,489, filed Oct. 25, 2002, which is incorporated herein by reference.

FIELD OF THE INVENTION

This invention relates to a process for synthesizing substantially enantiomerically pure amino acids, and will have application to a synthetic process for synthesizing the L-enantiomer of glutamic acid and substituted analogs thereof.

BACKGROUND OF THE INVENTION

It is well known in biochemistry that all amino acids exist in two three dimensional forms, which are virtual mirror images of each other. The two forms are referred to in the art by the direction in which they rotate polarized light-levorotatory (L) and dextrorotatory (D), respectively left and right. Fischer representations of the structural formulas for the two enantiomers of glutamic acid are depicted below.

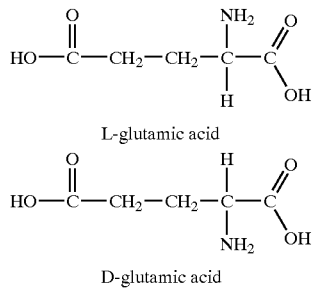

It is also well known that the L-enantiomer is the naturally occurring form of each amino acid found in nature. The L-enantiomer of each amino acid that forms a part of a drug agent is also the "active" enantiomer for medicinal purposes.

It is well known that antifolates which contain only the L-enantiomer of glutamic acid are much more active than those which include the D-enantiomer in a racemic mixture of the two enantiomers. The pure D-enantiomer of MDAM, as with most antifolates, is virtually inactive as a drug.

4'-methylene-4-[(2,4-diamino-3,4-dihydropteridin-6-yl) ethyl]-benzoyl-glutamic acid, also referred to as 4-deoxy-4-amino-10-deazapteroyl-γ-methylene glutamic acid, and as γ-methylene-10-deazaaminopterin (MDAM) is a well-known investigational antitumor agent. MDAM is currently undergoing human clinical trials in the United States and abroad as a treatment for cancer. MDAM and other antifolates are essentially "two-part" molecules, with a pteroic acid part and an amino acid part. When L-γ-methylene-glutamic acid forms the amino acid part, the agent is known as L-MDAM.

γ-methylene-L-glutamic acid is also a well-known depolarizing agent in the rat spinal cord. This property is suggestive of potent CNS activity, which may translate into the development of agents to treat various CNS disorders.

γ-methylene-L-glutamic acid has been isolated in substantially pure form from germinated peanuts as described in U.S. Pat. No. 5,550,128. The free acid form of γ-methylene-L-glutamic acid has been synthesized starting from L-pyroglutamic acid, as shown in the Ezquerra publication, appended to the Information Disclosure Sheet that accompanies this application.

γ-methylene-L-glutamic acid, which makes up the amino acid part of L-MDAM has been previously synthesized, through a previously unpublished process from a di-protected L-pyroglutamate starting material. The pyroglutamate is available commercially, and has also been synthesized by a previously unpublished process.

SUMMARY OF THE INVENTION

This invention involves a process for synthesizing substantially pure L-amino acids, as well as certain intermediate compounds. Primarily, the process of this invention will be used to synthesize substantially pure L-glutamic acid and intermediate compounds from which L-glutamic acid can be produced.

The process when employed to synthesize γ-methylene glutamic acid or an ester thereof includes derivatizing pyroglutamic acid or an ester thereof to add a methylene moiety; then decyclization of the pyroglutamate to form the linear glutamic acid or ester.

Derivatization of the pyroglutamate is accomplished by first protecting the nitrogen and carboxylic acid functional groups; then adding a γ-methylene moiety through a three-step procedure, which may be performed at or close to room temperature, and that may optionally be carried out in a single vessel. The preferred process is depicted in detail in the following Detailed Description.

It is an object of this invention to provide for a simple and improved process for synthesizing substantially pure L-glutamic acid and the like.

DESCRIPTION OF THE PREFERRED EMBODIMENT

The preferred embodiment herein described is not intended to be exhaustive or to limit the invention to the precise reagents, reaction steps or conditions disclosed. It has been chosen and described to explain the principles of the invention, and its application and practical use to thereby enable others skilled in the art to understand its teachings.

The process of this invention has as its primary objective the synthesis of substantially pure L-amino acids, most particularly the critical intermediate compound in the synthesis of the investigational anticancer drug, γ-methylene-10-deazaaminopterin (MDAM), whose structure is shown below:

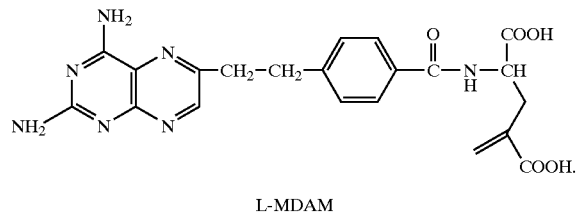

L-MDAM

As stated previously, L-MDAM is synthesized from two critical intermediates: (1) pteroic acid; and (2) γ-methylene-Lglutamic acid. The two intermediates are coupled via any of the known processes, with one such process being disclosed in U.S. Pat. No. 4,996,207, incorporated herein by reference. With slight modifications in the reagents used, similar L-amino acids may be synthesized by the process of this invention.

The process for synthesizing γ-methylene-L-glutamic acid is depicted in Scheme 1. As shown in Scheme 1, the process includes multiple steps in converting the starting material, a pyroglutamic acid derivative or an ester thereof, to the finished product, substantially enantiomerically pure γ-methylene-L-glutamic acid.

SCHEME 1

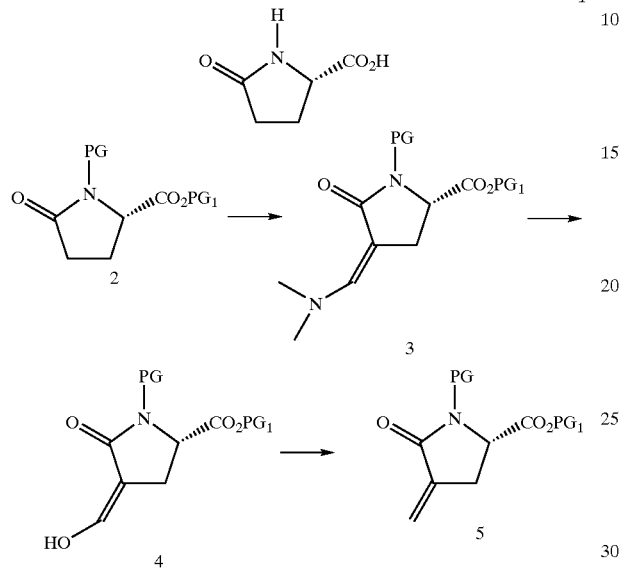

Scheme 1 illustrates the process of this invention as employed to synthesize 4-methylene-L-pyroglutamic acid 5. As shown, the preferred starting reagent is L-pyroglutamic acid 1. The process includes first protecting the nitrogen and carboxylic acid functional moieties to produce the diprotected pyroglutamate 2, wherein PG and $PG_1$ are commonly known protecting groups for nitrogen and carboxylic acid, respectively.

Protecting groups include specific moieties for protecting, in particular, nitrogen (amino) terminal moieties and oxygen (carboxylic acid) terminal moieties. Protecting groups are well known in the art and are described in detail in Kocienski, P., *Protecting Groups*, Foundations of Organic Chemistry (Thieme, 1994); and Greene, Wuts, *Protective Groups in Organic Synthesis* (Wiley, 2d ed. 1990), and in dozens of other reference publications.

Common protecting groups for nitrogen include t-butoxycarbonyl (t-BOC or BOC), 9-fluorenyl-methoxycarbonyl (FMOC) and others well known in the organic synthesis arts. Common protecting groups for carboxylic acid include lower alkyls, trimethylsilyl alkyls, and others well known in the organic synthesis arts. Methods for adding protecting groups were carried out using the well-known processes in the publications cited previously.

The protected pyroglutamate 2 is then converted to a 4-enamine 3, preferably by reacting with an amide, or most preferably a nitrogen-containing acetal. This conversion is preferably carried out at elevated temperatures, between 70° C to 130° C, most preferably between 105° C and 115° C. Enamine 3 is hydrolyzed, preferably with a strong acid, to the hydroxymethylene intermediate 4, then reduced in a basic solution to the desired product, the diprotected 4-methylene pyroglutamate 5. Detailed process steps and reagents, as well as preferred reaction conditions may be found in the specific examples, infra.

SCHEME 2

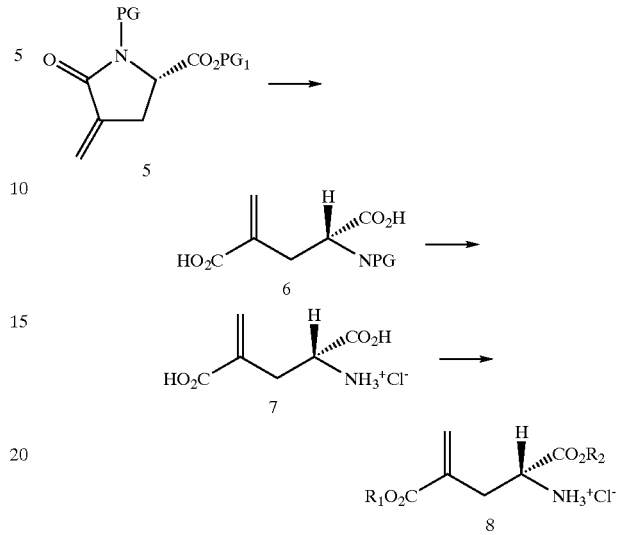

Scheme 2 illustrates the conversion of the 4-methylene pyroglutamate 5 to the preferred final product, 4-methylene-L-glutamic acid, and certain salts and esters thereof (6–8). A strong base is first reacted with the pyroglutamate 5, and is then followed by acidification of the resultant mixture to effect the conversion to the N-protected linear L-glutamic acid derivative (L-Glu) 6. Protected L-Glu 6 is deprotected by a common procedure to form L-Glu salt 7, and the salt is then esterified to produce the final product (8). $R_1$ and $R_2$ are oxygen-protecting agents, preferably lower ($C_1$–$C_6$) alkyl moieties.

The esterified L-Glu salt 8 may be used in the synthesis of L-MDAM by a coupling reaction of salt 8 to a pteroic acid derivative. The coupling reaction can be performed by any of a number of well-known procedures as outlined above.

The following specific examples illustrate the preferred process.

EXAMPLE 1

Ethyl-(2S)-pyroglutamate

To a solution of L-pyroglutamic acid (5.0 g) in ethanol (150 ml) was added 98% sulfuric acid (0.3 g). The resulting reaction mixture was stirred at room temperature for 48 hours. Sodium carbonate (1.5 g) was added and the stirring was continued for an additional 1.5 hours. The suspension was filtered and the filtrate was evaporated under reduced pressure. To the residue was added methyl t-butyl ether (MTBE-100 ml) and the resulting mixture was filtered. The filtrate was evaporated under reduced pressure to yield 6.5 g of the desired product as white solid.

EXAMPLE 2

Ethyl-(2S)-N-(t-butoxycarbonyl)pyroglutamate

To a solution of ethyl L-pyroglutamate (1.6 g), di(t-butyl) dicarbonate (2.4 g) and triethylamine (1.6 ml) in dichloromethane (7 ml) was added dimethylaminopyridine (DMAP-61 mg). The resulting mixture was stirred at room temperature overnight. The volatiles were removed under reduced pressure and the residue was taken up in MTBE (7 ml). The solid was removed by filtration and washed with fresh MTBE. The combined filtrates were washed with water (3 ml) and acidified to pH 3 with 1:9 v/v of dilute HCI. The resulting solution was washed with more water (2×3 ml). The organic phase was dried over sodium sulfate and activated carbon, filtered and evaporated under reduced pressure. The crude product was recrystallized from ether-hexanes to yield 1.65 g of product as white needles.

EXAMPLE 3

Ethyl-(2S)-4-(N,N-dimethylaminomethylidene)-N1-(t-butoxycarbonyl)pyroglutamate

A mixture of Ethyl (2S)-N-(tert-butoxycarbonyl) pyroglutamate (125 g, 486 mmol) and N, N-dimethyl formamide diisopropyl acetal (125 g, 713 mmol) was heated at 105–115° C for 21 hrs. Another portion of N, N-dimethyl formamide diisopropyl acetal (25 g, 143 mmol) was added and the solution was heated at 105–115° C for another 4 hrs. The solution was concentrated under reduced pressure at 70° C and dried at 70° C/0.3 mmHg until there is no bubbling. Crystallization from methyl t-butyl ether (250 ml) gave the named product as a white crystal (97 g, 64%): 1H NMR (300 Hz, $CDCl_3$) δ 7.06(t, 1H,J=1.8 Hz), 4.46 (dd, 1H,J=3.9, 10.5 Hz), 4.22–4.08 (m, 2 H), 3.32–3.14 (m, 1 H), 2.95 (s, 6 H), 2.89–2.78 (m, 1 H), 1.43 (s, 9 H), 1.21 (t, 3 H, J=7.2 Hz).

For this example, it is recommended to use 2 equivalents of N, N-dimethyl formamide diisopropyl acetal to each equivalent of pyroglutamate at the beginning. After 21 hrs of heating, Another 0.2 equivalent of N, N-dimethyl formamide diisopropyl acetal can be added if an HPLC analysis shows that the amount of starting material is great than 1.5 %.

EXAMPLE 4

Ethyl -(2S)4-methylene-N1 -(t-butoxycarbonyl) pyroglutamate

To a solution of ethyl (2S)-N-(t-butoxycarbonyl)-4-(dimethylaminomethylidene) pyroglutamate (100 g, 320.1 mmol) in tetrahydrofuran (THF-500 ml) was added 1 N HCI (352 ml). The mixture was stirred for 2 hours at room temperature. After separation, the organic layer was added potassium carbonate (62 g) and 37% formaldehyde (310 ml). The resulting solution was stirred at room temperature for 45 minutes, and the aqueous layer was separated. The organic layer was concentrated and the residue was taken up in MTBE (1000 ml). The resulting mixture was washed with water (380 ml), 20% $Na_2SO_3$ (380 ml) and water (380 ml), dried ($MgSO_4$) and evaporated to dryness in vacuo to yield the title product (71.7 g) as light yellow oil. This crude material was used as is in the next step.

EXAMPLE 5

4-methylene-N-(t-butoxycarbonyl)-L-glutamic acid

The crude product from Example 4 was dissolved in THF (650 ml) and to this solution was slowly added 2M LiOH (425 ml). The resulting mixture was stirred at room temperature for 48 hours. The aqueous layer was separated, acidified to pH 2 with 2N HCI, and extracted with ethyl acetate (2×500 ml). The extract was washed with water (250 ml) and dried ($MgSO_4$). The dried solution was used directly in the next step.

EXAMPLE 6

4-methylene-L-glutamic acid hydrochloride

To the dried solution from Example 4 was bubbled HCI (32.5 g over a period of 1 hour). The stirring was continued for an additional 1.5 hours after HCI was stopped. The resulting white solid was filtered, washed with MTBE (100 ml) and dried in vacuo to yield 31 g of substantially pure (>99%) of the title compound.

EXAMPLE 7

Diethyl 4-methylene-L-glutamate hydrochloride

4-Methylene L-glutamic acid hydrochloride (31 g) from Example 6 was dissolved in ethanol (310 ml). Thionyl chloride (31 ml) was added dropwise. The resulting mixture was stirred at room temperature overnight and then refluxed for 2.5 hours. The reaction mixture was concentrated to dryness. The crude product was dissolved in hot ethanol (31 ml) and to the hot solution was added anhydrous MTBE (620 ml). The resulting mixture was kept at room temperature overnight. The crystals of the product were filtered and dried in vacuo to yield 34 g of substantially pure (>99%) title compound. The enantiomeric purity of the final product is 99.5% as verified in a chiral AGP column, 4 mM PBS (pH 6), isopropanol=98.5:1.5.

What is claimed is:

1. A process for synthesizing greater than 99% enantiomerically pure 4-methylene-L-glutamic acid or an ester thereof having the formula

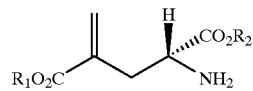

wherein $R_1$ and $R_2$ are individually hydrogen or $C_1$–$C_6$ alkyl, said process comprising the steps of:

a. providing a protected (2S)-pyroglutamic acid or ester thereof as a starting material;

b. reacting the starting material with an amide or an acetal at a temperature ranging from 70° C to 130° C to form a protected 4-enamine pyroglutamic acid intermediate or ester thereof;

c. hydrolyzing the protected 4-enamine derivative to form a protected 4-hydroxymethylidene pyroglutamic acid intermediate or ester thereof;

d. reducing in a basic solution the protected 4-hydroxymethylidene intermediate to form a protected 4-methylene pyroglutamic acid or an ester thereof; and e. reacting the protected 4-methylene pyroglutamic acid with a base to form linear 4-methylene glutamic acid, or an ester or salt thereof.

2. The process of claim 1 wherein step b includes reacting the starting material with an acetal at a temperature ranging from 105° C to 115° C.

3. The process of claim 1 wherein step c includes reacting the protected 4-enaine intermediate with a strong acid.

4. The process of claim 1 wherein step d includes reacting the protected 4-hydroxymethylidene intermediate with a carbonate salt.

5. The process of claim 1 wherein the base is lithium hydroxide.

* * * * *